United States Patent [19]

Kay et al.

[11] Patent Number: 4,506,084
[45] Date of Patent: Mar. 19, 1985

[54] AMINONITRILE INTERMEDIATES

[75] Inventors: Ian T. Kay, Wokingham; Robert A. Noon, London, both of England

[73] Assignee: Imperial Chemical Industries PLC, London, England

[21] Appl. No.: 555,541

[22] Filed: Nov. 28, 1983

Related U.S. Application Data

[62] Division of Ser. No. 356,801, Mar. 10, 1982, Pat. No. 4,432,784.

[30] Foreign Application Priority Data

Mar. 19, 1981 [GB] United Kingdom ............... 8108676

[51] Int. Cl.³ .................. C07D 307/52; C07D 333/24
[52] U.S. Cl. .................................. 549/74; 549/75; 549/492; 549/495
[58] Field of Search ............... 549/74, 75, 492, 495

[56] References Cited

U.S. PATENT DOCUMENTS

| | | | |
|---|---|---|---|
| 3,901,917 | 8/1975 | Richter et al. | 71/90 X |
| 3,995,044 | 11/1976 | Kabbe et al. | 549/77 X |
| 4,029,653 | 6/1977 | Dolfini | 544/21 |
| 4,072,698 | 2/1978 | Hylton et al. | 549/74 X |

FOREIGN PATENT DOCUMENTS

| | | |
|---|---|---|
| 667679 | 12/1981 | Japan . |
| 1395802 | 5/1975 | United Kingdom . |
| 1498199 | 1/1978 | United Kingdom . |
| 2000140 | 1/1979 | United Kingdom . |

OTHER PUBLICATIONS

Dolfini, Chemical Abstracts, vol. 86, (1977), 189981k.
Krauch et al., Reaktionen der Organischen Chemie, Dr. Alfred Huthig Verlag, Heidelberg, 1976, pp. 142–144.

*Primary Examiner*—Richard L. Raymond
*Attorney, Agent, or Firm*—Cushman, Darby & Cushman

[57] ABSTRACT

N-Heterocyclylmethyl amides of the formula (I)

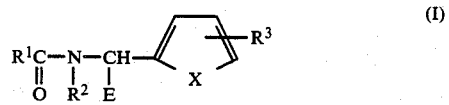

wherein
  $R^1$ is an optionally substituted alkyl, alkenyl, aryl, or heterocyclyl radical;
  $R^2$ is hydrogen, or an optionally substituted $C_{1-4}$ alkyl, or $C_{3-4}$ alkenyl group;
  E is —CN, —CSNH$_2$, alkoxycarbonyl, or a —CONR$^4$R$^5$ group wherein $R^4$ and $R^5$ may each be hydrogen or an optionally substituted alkyl or alkenyl radical;
  X is oxygen or sulphur, and
  $R^3$ represents hydrogen or one or more substituents which may be for example methyl or chlorine.

The compounds are herbicidally and fungicidally active.

1 Claim, No Drawings

AMINONITRILE INTERMEDIATES

This is a division of application Ser. No. 356,801 filed Mar. 10, 1982, now U.S. Pat. No. 4,432,784.

This invention relates to certain N-heterocyclyl methyl amide derivatives useful as herbicides and fungicides, to processes of combatting weeds and fungal infestations, and to herbicidal and fungicidal compositions.

Substituted benzamide derivatives have previously been proposed for use as herbicides. By way of example, the compounds disclosed in U.K. Patent Specifications Nos. 1209608 and 1395802 may be mentioned.

According to the present invention, there are provided N-heterocyclylmethyl amides of the formula (I)

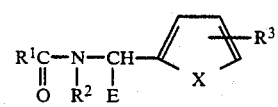

wherein $R^1$ is an optionally substituted alkyl, alkenyl, aryl, or heterocyclyl radical;

$R^2$ is hydrogen, or an optionally substituted $C_{1-4}$ alkyl, or $C_{3-4}$ alkenyl group;

E is —CN, —CSNH$_2$, alkoxycarbonyl, or a —CONR$^4$R$^5$ group wherein $R^4$ and $R^5$ may each be hydrogen or an optionally substituted alkyl or alkenyl radical;

X is oxygen or sulphur, and $R^3$ represents hydrogen or one or more substituents which may be for example methyl or chlorine.

When $R^1$ is alkyl or alkenyl it may for example be an alkyl radical of 3 to 5 or more carbon atoms or an alkenyl radical of 3 to 5 or more carbon atoms. When $R^1$ is a substituted alkyl or alkenyl radical there may be one or more substituents. Examples of substituents include halogen (e.g. chlorine or fluorine), alkoxy (e.g. $C_1$-$C_4$ alkylthio).

When $R^1$ is aryl it may be for example phenyl or naphthyl. When the aryl group is substituted, there may be one to three or more substituents. Examples of substituents include alkyl (e.g. $C_1$-$C_3$ alkyl), halogen (e.g. $C_1$-$C_3$ alkoxy), haloalkoxy (e.g. $CF_3O$—) nitro, cyano, methylene dioxy, and haloalkyl (e.g. $CF_3$).

When $R^1$ is a heterocyclic group it may be for example a 2-furyl, 2-thienyl, or 4-pyridyl group. When $R^1$ is a substituted heterocyclic group there may be from one to three or more substituents. Examples of substituents include those listed above for the case when $R^1$ is aryl.

When $R^2$ is alkyl it may be for example alkyl of 1 to 4 carbon atoms. When $R^2$ is alkenyl it may be for example alkenyl of 3 to 5 carbon atoms. When $R^2$ is substituted alkyl or alkenyl, there may be one or more substituents. Examples of substituents include $C_1$-$C_4$ alkoxy, $C_1$-$C_4$ alkylthio, and halogen (e.g. chlorine and fluorine).

When E is alkoxycarbonyl it may be alkoxycarbonyl of 2 to 4 carbon atoms.

When E is a —CONR$^4$R$^5$ group, each of the groups $R^4$ and $R^5$ may be, for example, hydrogen or $C_1$-$C_4$ alkyl.

Within the foregoing definition, one subgroup of compounds according to the invention comprises compounds in which $R^1$ is substituted phenyl, $R^2$ is hydrogen, and E is CN. Within this sub-group, a further class of compounds comprises those in which the substituents in the phenyl group are located in the 3-, 4- or the 5-position of the phenyl ring. Within this class, a further sub-class comprises compounds in which X is oxygen, and $R^3$ is hydrogen.

The structural formula (I) given above is believed to be the one which best represents the structure of the compounds. For some compounds within the scope of the formula (I) it may be possible in principle for tautomeric forms of the compound to exist, in which a hydrogen atom is transposed to another part of the molecule and the chemical bonds between the atoms of the molecule are consequently re-arranged; thus, where $R^2$ is hydrogen, it is possible in principle for the molecule to exist in the alternative form (IA).

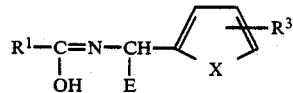

The structural formula (I) is intended to represent and include such tautomeric forms, insofar as they may exist. The structural formula (I) is also intended to include any physically distinguishable modifications of the compounds which may arise, for example, from different ways in which the molecules are arranged in a crystal lattice, or from the inability of parts of the molecules to rotate freely in relation to other parts, or from geometrical isomerism, or from intra-molecular or inter-molecular bonding, or otherwise.

Particular examples of compounds according to the invention are listed in Table 1 below:

TABLE 1

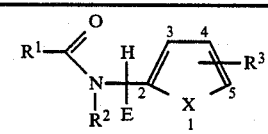

| COMPOUND NO | $R^1$ | $R^2$ | E | X | $R^3$ | ROUTE | MELTING POINT °C. |
|---|---|---|---|---|---|---|---|
| 1 | $C_6H_5$ | H | CN | O | H | A | 116–118 |
| 2 | 3-Cl.$C_6H_4$. | H | CN | O | H | A | 103–104 |
| 3 | 2,6-Me$_2$.$C_6H_3$. | H | CN | O | H | A | 143–144 |
| 4 | 3,5-Cl$_2$.$C_6H_3$. | H | CN | O | H | A | 153–155 |
| 5 | 3-Me.$C_6H_4$. | H | CN | O | H | A | 104–105 |
| 6 | 3,5-Me$_2$.$C_6H_3$. | H | CN | O | H | A | 141–143 |
| 7 | 3,5-Cl$_2$.$C_6H_3$ | H | CSNH$_2$ | O | H | D | 158–160 |
| 8 | 3-Cl.$C_6H_4$. | Me | CN | O | H | A | 52–53 |
| 9 | 3-Me.$C_6H_4$. | Me | CN | O | H | A | 38–39 |

TABLE 1-continued

| COMPOUND NO | R¹ | R² | E | X | R³ | ROUTE | MELTING POINT °C. |
|---|---|---|---|---|---|---|---|
| 10 | 3-F.C₆H₄. | H | CN | O | H | A | 88–90 |
| 11 | isoC₄H₉. | Me | CN | O | H | A | Oil ($N_D^{21}$ = 1.4861) |
| 12 | 3-F.C₆H₄. | Me | CN | O | H | A | Oil ($N_D^{21}$ = 1.5408) |
| 13 | isoC₄H₉. | H | CN | O | H | A | 80–81 |
| 14 | 3,5-Me₂.C₆H₃. | Me | CN | O | H | A | 73–75 |
| 15 | 3,5-Cl₂.C₆H₃. | Me | CN | O | H | A | 65–67 |
| 16 | 3,5-Cl₂.C₆H₃. | H | CN | S | H | A | 173–175 |
| 17 | 3-Cl.C₆H₄. | H | CN | S | H | A | 100–102 |
| 18 | C₆H₅. | H | CSNH₂ | O | H | D | 181–183 |
| 19 | 2,6-dichloro-4-pyridyl | H | CN | O | H | A | 134–135 |
| 20 | 3-MeO.C₆H₄. | H | CN | O | H | A | 77–79 |
| 21 | 3-MeO.C₆H₄. | H | CSNH₂ | O | H | D | 132–133 |
| 22 | 3,5-(MeO)₂.C₆H₃. | H | CN | O | H | A | 130–132 |
| 23 | 2-furyl | H | CN | O | H | A | 82–83 |
| 24 | 2-chloro-5-thienyl | H | CN | O | H | A | 130–132 |
| 25 | t-C₄H₉. | H | CN | O | H | A | 68–69 |
| 26 | 3,5-Cl₂.C₆H₃. | H | CO₂Me | S | H | C | 68–69 |
| 27 | Benzo (b) furan-2-yl | H | CN | O | H | A | 94–96 |
| 28 | iso.C₅H₁₁ | H | CN | O | H | A | 71–72 |
| 29 | 2-naphthyl | H | CN | O | H | A | 114–117 |
| 30 | 5-bromo-2-furyl | H | CN | O | H | A | 105–107 |
| 31 | 3,4-Cl₂.C₆H₃. | H | CN | O | H | A | 124–126 |
| 32 | 3,5-F₂.C₆H₃. | H | CN | O | H | A | 130–131 |
| 33 | 4-chloro-2-thienyl | H | CN | O | H | A | 118–119 |
| 34 | 4-Cl.C₆H₄. | H | CN | O | H | A | 117–118 |
| 35 | 4-F.C₆H₄. | H | CN | O | H | A | 85–86 |
| 36 | (CH₃)₂CHCH=CH— | H | CN | O | H | A | 109–110 |
| 37 | C₆H₅ | H | CN | O | 5-Me | A | 132–133 |
| 38 | 3,5-Me₂.C₆H₃ | H | CN | O | 5-Me | A | 125–126 |
| 39 | 3-F.C₆H₄. | H | CN | O | 5-Me | A | 87–88 |
| 40 | 3,5-Cl₂.C₆H₃. | H | CN | O | 5-Me | A | 128–129 |
| 41 | 3,5-Cl₂.C₆H₃. | H | CONH₂ | O | H | E | 215–217 |
| 42 | 4-Cl.C₆H₄. | H | CN | O | 5-Me | A | 150–151 |
| 43 | 3,4-Cl₂.C₆H₃. | H | CN | O | 5-Me | A | 108–110 |
| 44 | 4-Me.C₆H₄. | H | CN | O | 5-Me | A | 137–138 |
| 45 | 3,5-Cl₂.C₆H₃. | H | CO₂Me | O | H | C | 108–110 |
| 46 | 3,5-F₂.C₆H₃. | H | CN | O | 5-Me | A | 116–118 |
| 47 | 3,4,5-F₃.C₆H₂. | H | CN | O | H | A | 132–134 |
| 48 | C₆H₅. | Me | CN | O | H | B | Oil |
| 49 | 4-F.C₆H₄ | H | CN | S | H | A | 85–87 |
| 50 | 2-Furyl | H | CN | S | H | A | 98–99 |
| 51 | 2-F.C₆H₄ | H | CN | S | H | A | 113–115 |
| 52 | 3,4,5-F₃C₆H₂ | H | CN | S | H | A | 108–110 |
| 53 | 4-ClC₆H₄ | H | CN | S | H | A | 100–102 |
| 54 | 3-FC₆H₄. | H | CN | S | H | A | 133–135 |
| 55 | 2-FC₆H₄ | H | CN | O | H | A | 102–103 |
| 56 | 3,5-F₂C₆H₃ | H | CN | S | H | A | 145–147 |
| 57 | 3,4-OCH₂OC₆H₃ | H | CN | O | H | A | 146–148 |
| 58 | ClCH₂ | Me | CN | O | H | A | 47–49 |
| 59 | 2-Furyl | Me | CN | O | H | A | 32–34 |
| 60 | Cl₃C | Me | CN | O | H | A | 82–84 |
| 61 | 4-MeOC₆H₄ | H | CN | O | H | A | 108–109 |
| 62 | 3,4-(MeO)₂C₆H₃ | H | CN | O | H | A | 158–159 |
| 63 | 2-Furyl | allyl | CN | O | H | A | 39–41 |
| 64 | 4-MeC₆H₄ | H | CN | O | H | A | 132–134 |
| 65 | 3,5Cl₂C₆H₃ | allyl | CN | O | H | A | 50–52 |
| 66 | 3-Cl—4-MeOC₆H₃ | H | CN | O | H | A | |
| 67 | 4-CF₃C₆H₄ | H | CN | O | H | A | |
| 68 | 4-BrC₆H₄ | H | CN | O | H | A | |
| 69 | 3-Cl—4-MeC₆H₃ | H | CN | O | H | A | |
| 70 | 4-CNC₆H₄ | H | CN | O | H | A | |
| 71 | 3,4-(Me)₂C₆H₃ | H | CN | O | H | A | |
| 72 | 3,4,5(Me)₃C₆H₂ | H | CN | O | H | A | |
| 73 | 4-Cl—3-MeC₆H₃ | H | CN | O | H | A | |
| 74 | 4-Me—3,5-Cl₂C₆H₂ | H | CN | O | H | A | |

In another aspect the invention provides a process of inhibiting the growth of unwanted plants, which comprises applying to the plants, or to the locus thereof, a phytotoxic amount of a compound of the formula (I) as hereinbefore defined. The amount of the compound may vary, depending upon the identity of the particular compound chosen and the plant species whose growth is to be inhibited, but in general amounts of from 0.01 to 5.0 kilograms per hectare will be suitable; usually the amount will be from 0.2 to 1.0 kilograms per hectare. The skilled worker in the herbicide art will readily be able to establish appropriate application rates by standard procedures without undue experimentation.

The compounds of the invention are relatively less toxic towards certain crop plants than they are towards other plant species; accordingly, there is the possibility of using the compounds for selective weed control in these crops. Examples of such crops include cotton, sugar beet, rape, lettuce, peas; the compounds may be useful in a number of crops of the families Compositae and Leguminosae.

The compounds used in the process of the invention are preferably applied in the form of a composition, in which the active ingredient is mixed with a carrier comprising a solid or liquid diluent. In another aspect, therefore, the invention provides a herbicidal composition, comprising as an active ingredient a compound of the formula (I) as hereinbefore defined, in admixture with a solid or liquid diluent. Preferably the composition also comprises a surface-active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's Earth.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl- and triisopropyl-naphthalenesulphonic acid. Suitable agents of the non-ionic type include, for example, the condensation products of ethylene oxide with fatty alcohols such as oleyl alcohol and cetyl alcohol, or with alkyl phenols such as octyl-phenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogenous for a sufficient time to enable them to be applied by conventional spray equipment.

The compositions of the invention may contain, in addition to carriers and surface-active agents, various other constituents to increase their usefulness. They may contain, for example, buffering salts to maintain the pH of the composition within a desired range; antifreeze agents, for example urea or propylene glycol; adjuvants, for example oils and humectants; and sequestrants, for example citric acid and ethylenediaminetetracetic acid, which help to prevent the formation of insoluble precipitates when the compositions are diluted with hard water. Aqueous dispersions may contain anti-settling agents and anti-caking agents. The compositions may in general contain a dye or pigment to impart a characteristic colour. Agents for increasing viscosity may be added to reduce the formation of fine droplets during spraying, and thereby reduce spray drift. Other additives useful for particular purposes will be known to those skilled in the formulation art.

In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient.

The invention further provides processes for preparing compounds of formula (I) above. Thus, the compounds may be prepared by the process of Route A, below.

Route A (a) 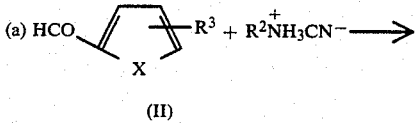

(II)

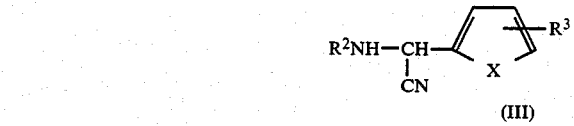

(III)

(b) (III) + $R^1COCl \longrightarrow$ 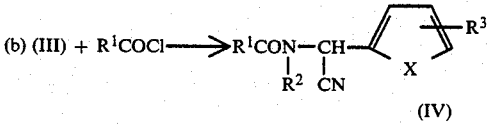

(IV)

In Route A, an aldehyde derivative (II) is reacted with an amine $R^2NH_2$ in the presence of HCN under the conditions of the Strecker reaction to give the cyano derivative (III). This is then treated with an acid chloride R¹COCl in the presence of an acid acceptor to give the required compound (IV).

A further process for preparing compounds of the invention is outlined in Route B below:

Route B (a) (II) + R²NH₂ ⟶ 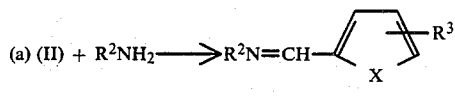

(V)

(b) (V) + R¹COCN ⟶ (IV)

In Route B, the aldehyde derivative (II) is reacted with a primary amine R²NH₂ to form the imine (V). The reaction may be carried out in a solvent (e.g. a lower alkanol) at ambient temperature and the imine isolated by removal of the solvent. The imine (V) is then reacted with an acyl cyanide R¹COCN to give the required compound (IV). The reaction is conveniently carried out in a solvent for the reactants. Suitable solvents are aprotic solvents, for example ether. The reaction may be carried out at ambient temperatures.

A further process for preparing compounds according to the invention is outlined as Route C below:

Route C (a) R¹CONH₂ + HCOCO₂R⁶ ⟶ R¹CONH CH(OH)CO₂R⁶
                                          (OAc)

(VI)

(b) (VI) + 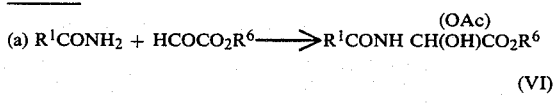 (VIII)

(c) (VIII) + NH₃ ⟶ 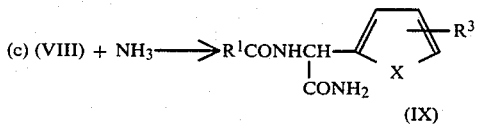

(IX)

(d) (IX) —dehydrating agent→ 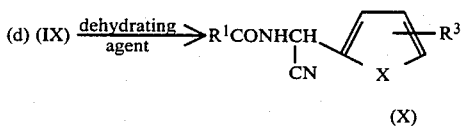

(X)

In Route C, an amide R¹CONH₂ is reacted with an ester of glyoxylic acid HCOCO₂R⁶ (R⁶ is an esterifying radical, for example a lower alkyl radical, e.g. methyl) to give the hydroxy-amide derivative (VI). The reaction is conveniently carried out in a solvent (e.g. an ester, for example ethyl acetate) and may be accelerated by heating (e.g. at 50°–120° C., more especially at 70°–100° C.). The hydroxy-amide (VI) so obtained is then reacted in Step (b) with the heterocyclic derivative (VII) in the presence of a Lewis acid (e.g. boron trifluoride etherate) to form the ester (VIII). Preferably the hydroxy-amide (VI) is first converted to its acetoxy derivative (e.g. by treatment with thionyl chloride followed by sodium acetate in glacial acetic acid) before Step (b) is carried out.

The ester (VIII) so prepared is next converted to the corresponding amide (IX) by treatment in solution with ammonia according to well known procedure. The amide (IX) may then be dehydrated by treatment with a conventional dehydrating agent (e.g. POCl₃) to form the nitrile (X).

A further process for preparing compounds according to the invention wherein E is a —CSNH₂ group is outlined in Route D below:

Route D

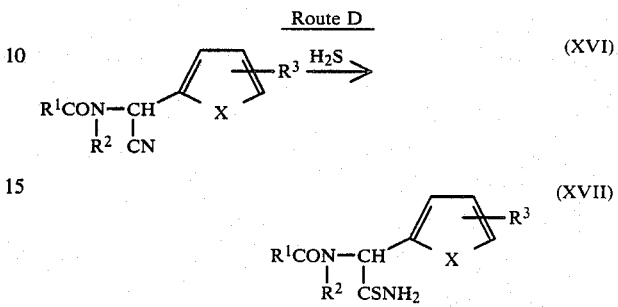

In Route D, a compound (XVI) according to the invention wherein the group E is a cyano group is treated in solution with gaseous hydrogen sulphide, in the presence of a catalytic amount of a tertiary amine (e.g. triethylamine) to give the corresponding compound (XVII) in which the group E is a thiocarbamoyl group.

A further process for preparing compounds according to the invention is outlined as Scheme F below:

Route E

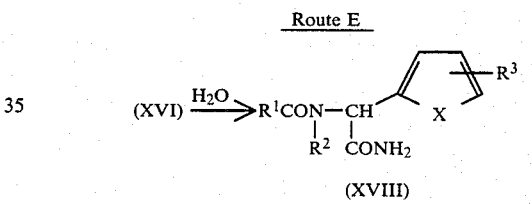

Route E provides a method whereby compounds according to the invention in which E is a carbamoyl group may be prepared from compounds in which E is cyano. The reaction may be carried out in various ways according to known procedures for converting cyano groups into carbamoyl groups; for example, the cyano compound (XVI) may be treated with a mixture of an alkali (e.g. sodium hydroxide solution) and hydrogen peroxide.

The invention in a further aspect, embraces the novel intermediates set out in relation to the foregoing processes of the invention.

The amide derivatives of formula I, and compositions containing them, are variously active against a wide range of fungal diseases, particularly, for example, against:

*Plasmopara viticola* (downy mildew) on vines and
*Phytophthora infestans* (late blight) on potatoes and tomatoes
Other fungal diseases, for example:
*Venturia inaequalis* (scab) on apples
*Cercospora arachidicola* on peanuts and other
Cercospora species.

A particularly valuable feature of the activity of the amide derivatives is their systemic effect, i.e. their ability to move in a plant to combat an infection or infestation remote from the site of initial application. Thus a derivative, or a composition containing it, may be applied to the soil surrounding the roots of a plant or to the seed or to other plant areas, e.g. leaves, and be taken up by the plant through its roots, or other areas, to combat fungi locally or elsewhere on the plants.

In another aspect, therefore, the invention provides a process for combatting fungi, especially of inhibiting the growth of fungi on plants, which comprises applying to the plants, or the locus thereof, a fungicidally effective amount of a compound of the formula (I) as hereinbefore defined. The amount of the compound may vary, depending upon the identity of the particular compound chosen, the fungal species whose growth is to be inhibited, and the plant or locus involved. The skilled worker in the fungicide art will readily be able to establish appropriate application rates by standard procedures without undue experimentation.

Preferred compounds for use in the fungicidal compositions of the invention and the process for combatting fungi are those defined in detail above with reference to formula I wherein $R_2$ is hydrogen, $R^1$ is optionally-substituted phenyl, or heterocyclyl, X is O or S, $R^3$ is hydrogen or alkyl and E is Cn, $CSNH_2$, alkoxycarbonyl, or $CONR^4R^5$.

An even more preferred group of compounds are those wherein R is optionally substituted phenyl, $R^2$ is hydrogen, X is oxygen and $R^3$ is hydrogen and E is CN.

The compounds used in the process and compositions of the invention are preferably applied in the form of a composition, in which the active ingredient is mixed with a carrier comprising a solid or liquid diluent. In another aspect, therefore, the invention provides a fungicidal composition, comprising as an active ingredient a compound of the formula (I) as hereinbefore defined, in admixture with a solid or liquid diluent. Preferably the composition also comprises a surface-active agent.

The amide derivatives may be used as such for antifungal purposes but are more conveniently formulated into compositions for such usage.

The invention also provides fungicidal compositions comprising as active ingredient an amide derivative as defined in any of the paragraphs above.

The amide derivatives and compositions containing them can be used to combat plant fungi and treat plants or seeds in a number of ways, for example they can be applied, formulated or unformulated, directly to the foliage of a plant which is infected or likely to become infected, or they can be applied also to bushes and trees, to soil or to other medium in which plants, bushes or trees are growing or to be planted, or they can be sprayed on, dusted on or applied as a cream or paste formulation. Application can be to any part of the plant, bush or tree, for example to the foliage, stems, branches, seeds or roots, or to the soil surrounding the roots.

The terms "combatting" and "treatment" as used herein embrace all the foregoing modes of application and the term "plant" includes seedlings, bushes and trees. Furthermore, the method of the invention includes protectant, prophylactic and eradicant treatment.

The derivatives are preferably used for agricultural and horticultural purposes in the form of compositions. The type of composition used in any instance will depend upon the particular purpose envisaged.

The compositions may be in the form of dusting powders or granules, for example ordinary grains or "slow release" granules wherein the active ingredient is mixed with a solid diluent or carrier, for example, kaolin, bentonite, kieselguhr, dolomite, calcium carbonate, talc, powdered magnesia, Fuller's earth, gypsum, Hewitt's earth, diatomaceous earth and China clay.

Compositions for dressing seed may, for example, comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersion of emulsions may be prepared by dissolving the active ingredient(s) in an organic solvent which may contain wetting, dispersing or emulsifying agent(s) and then adding the mixture so obtained to water which may also contain wetting, dispersing or emulsifying agent(s). Suitable organic solvents are ethylene dichloride, isopropyl alcohol, propylene glycol, diacetone alcohol, toluene, kerosene, methylnaphthalene, xylenes and trichloroethylene.

The compositions for spraying may also be in the form of aerosols wherein the formulation is held in a propellant, e.g. fluorotrichloromethane or dichlorodifluoromethane.

By including suitable additives, for example additives for improving the distribution, adhesive power and resistance to rain on treated surfaces, the different compositions can be better adapted for various utilities.

The derivatives can be used in smoke generators and also as mixtures with fertilisers (e.g. nitrogen- or phosphorus-containing fertilisers). Compositions comprising only granules of fertiliser incorporating, for example coated with, the derivative, are preferred.

The invention therefore also provides a fertiliser composition comprising the derivative and a fertiliser.

The compositions may also be in the form of liquid preparations for use as dips or sprays which are generally aqueous dispersions or emulsions containing the active ingredient in the presence of one or more surface active agent(s), dispersing agent(s), emulsifying agent(s) or anionic or non-ionic agents. Suitable cationic agents are quaternary ammonium compounds for example, cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzene-sulphonate, sodium, calcium or ammonium lignosulphonate, butylnaphthalene sulphonate, and a mixture of sodium di-isopropyl- and triisopropylnaphthalene sulphonates).

Suitable non-ionic agents are the condensation products of ethylene oxide with fatty alcohols such as oleyl alcohol or cetyl alcohol, or with alkyl phenols such as octylphenol, nonylphenol and octylcresol. Other nonionic agents are the partial esters derived from long chain fatty acids and hexitol anhydrides, the condensation products of the said partial esters with ethylene ocide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such form aqueous preparations which remain homogenous for a sufficient time to enable them to be applied by conventional spray equipment. The concentrates may conveniently contain 10–85%, generally 25–60%, by weight of the active ingredient(s).

When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, for example other fungicides such as dithiocarbamates, dinocap, dichlofluanid and the like, as well as stabilising agent(s), for example epoxides (e.g. epichlorhydrin).

The invention is illustrated by the following Examples, in which unless otherwise stated all parts are by weight and temperatures in degrees Centigrade. The Examples that describe chemical syntheses give details in some cases of the nuclear magnetic resonance (NMR) spectra of the compounds. The information given is the chemical shift (δ) for each peak in the spectrum together with a symbol to indicate the nature of the peak, as follows: s(singlet); d(doublet); m(multiplet); q(quartet); t(triplet). The solvent used was fully deuterated dimethyl sulphoxide or deuterochloroform ($CDCl_3$).

EXAMPLE 1

This Example illustrates the preparation of benzoylamino-(2-furyl)acetonitrile (Compound No 1 of Table 1) by Route A.

Using the general method described by Goldberg and Kelly for 1-aminoethyl cyanide (J.Chem.Soc.,1947, 1371), furfural was converted to 2-amino-2-furylacetonitrile hydrochloride. To a solution of this hydrochloride (2.0 g) in water (15 ml) was added caustic soda (1.11 g) and benzoyl chloride (1.77 g) and the mixture shaken for 15 minutes. The product (0.7 g) was separated, washed with water, dried, and crystallised from carbon tetrachloride when it had m.p. 116°–118°.

Found: C, 68.61; H, 4.53; N, 12.16; $C_{13}H_{10}N_2O_2$ requires: C, 69.03; H, 4.43; N, 12.39%.

EXAMPLE 2

This Example illustrates the preparation of N-methylbenzoylamino-(2-furyl)acetonitrile (Compound No 48 of Table 1) by Route B.

To a stirred solution of furfural (5 g) in ethanol (50 ml) was added dropwise methylamine (4.89 g of a 33% solution in ethanol). After allowing the mixture to stand overnight at room temperature the solvent was removed under reduced pressure and the residual oily imine distilled at 0.1 mm.

The imine (1.0 g) in anhydrous ether (20 ml) was treated with benzoyl cyanide (1.21 g) and the mixture kept, protected from moisture, for 48 hours. Removal of the ether left a red oil which was chromatographed on a column of silica using diisopropyl ether as an eluent. Removal of the solvent following elution from the column gave the product as a pale yellow oil (1.11 g).

δ ($CDCl_3$): 3.0 (3H,s), 6.45 (1H,m), 6.65 (1H,m), 6.85 (1H,s,broad), 7.5 (6H,m).

EXAMPLE 3

This Example illustrates the preparation of methyl (3,5-dichlorobenzoylamino)-2(2-furyl)acetate (Compound No 45 of Table 1) by Route C.

A mixture of 3,5-dichlorobenzamide (19.0 g) and methyl glyoxylate (8.8 g) in ethyl acetate (300 ml) was heated under reflux for 8 hours. The solvent was removed and the residue crystallised from chloroform-light petroleum. A sample of the resultant hydroxy ester (3.0 g) was dissolved with stirring in thionyl chloride (100 ml), and after the solid had dissolved (ca. 2 hours) the excess of thionyl chloride was removed under reduced pressure. The residual solid was dissolved in glacial acetic acid (50 ml) containing anhydrous sodium acetate (2.0 g) and the mixture allowed to stand for 4 hours. The acetic acid was removed under reduced pressure and water (50 ml) added to the residue. The solid was separated, dried, and crystallised from light petroleum to give methyl acetoxy-(3,4-dichlorobenzoylamino)acetate (2.0 g).

The foregoing acetoxyamide (1.0 g) was dissolved in ether (30 ml) containing furan (5 ml) and then treated with boron trifluoride etherate (1 ml) whereupon the mixture was kept at room temperature for 5 days. The solution was washed with water, the ether layer dried ($MgSO_4$) and evaporated. Crystallisation of the residual solid from light petroleum gave the product (0.5 g) as a colourless crystalline solid, m.p. 108°–110°.

Found: C, 51.36; H, 3.74; N, 4.16; $C_{14}H_{11}Cl_2NO_4$ requires: C, 51.22; H, 3.35; N, 4.26%. δ($CDCl_3$): 3.8 (3H,s), 5.9 (1H,d), ca. 6.4 (2H,m), 7.1–7.8 (5H,m).

EXAMPLE 4

This Example illustrates the preparation of 3,5-dichlorobenzoylamino-2-furylthioacetamide (Compound No 7 of Table 1) by Route D.

Hydrogen sulphide was passed for 1 hour into a suspension of 3,5-dichlorobenzoylamino-2-furylacetonitrile (1.68 g) in toluene (100 ml) containing triethylamine (10 ml). The solvent was removed under reduced pressure and the residual solid crystallised from chloroform-hexane to give the product (1.4 g) as a colourless crystalline solid, m.p. 158°–160°.

EXAMPLE 5

This Example illustrates the preparation of 3,5-dichlorobenzoylamino-2-furylacetamide (Compound No 41 of Table 1) by Route E.

A mixture of 3,5-dichlorobenzoylamino-2-furylacetonitrile (0.5 g), sodium hydroxide (0.075 g) and hydrogen peroxide (equivalent to 0.092 g) in water (10 ml) and methanol (15 ml) was heated at 55°–60° for 1 hour. The solution was cooled, the solid separated, washed with water, dried and crystallised from ethyl acetate-light petroleum to give the product (0.35 g), m.p. 215°–217°.

Found: C, 48.68; H, 3.3; N, 8.61; $C_{13}H_{10}Cl_2N_2O_3$ requires: C, 48.84; H, 3.19; N, 8.95%

EXAMPLE 6

This Example illustrates the herbicidal activity of compounds of the invention. The compounds were submitted to herbicide tests as described below:

Each compound was formulated for test by mixing an appropriate amount of it with 5 ml of an emulsion prepared by diluting 160 ml of a solution containing 21.8 grams per liter of Span 80 and 78.2 grams per liter of Tween 20 in methylcyclohexanone to 500 ml with water. Span 80 is a Trade Mark for a surface-active agent comprising sorbitan monolaurate. Tween 20 is a Trade Mark for a surface-active agent comprising a condensate of 20 molar proportions of ethylene oxide with sorbitan monolaurate. The mixture of the compound and the emulsion was then shaken with glass beads and diluted to 44 ml with water. The spray composition so prepared was sprayed on to young pot plants (post-emergence test) of the species named in Tables 2 and 3 below, at a rate equivalent to 1000 liters per hectare. Damage to plants was assessed 13 days after spraying by comparison with untreated plants, on a scale of 0 to 5 where 0 is 0 to 20% damage and 5 is complete kill. In the table of results, a dash (—) means no test was made.

A test was also carried out to detect pre-emergence herbicidal activity. Seeds of the test species were placed on the surface of fibre trays of soil and were sprayed with the compositions at the rate of 1000 liters per hectare. The seeds were then covered with further soil. 20 days after spraying, the seedlings in the sprayed fibre trays were compared with the seedlings in unsprayed control trays, the damage being assessed on the same scale of 0 to 5.

The results of the tests are given in Tables 2 and 3 below.

TABLE 2

| COMPOUND NO | RATE OF APPLICATION kg/ha | PRE- OR POST-EMERGENCE APPLICATION | TEST PLANTS | | | | | | | | | | | |
|---|---|---|---|---|---|---|---|---|---|---|---|---|---|---|
| | | | Sb | Rp | Ct | Sy | Mz | Ww | Rc | Sn | Ip | Am | Pi | Ca |
| 1 | 1.0 | Pre | 0 | 4 | 2 | 4 | 1 | 5 | 0 | 4 | 1 | 0 | 0 | 0 |
| | | Post | 1 | 1 | 1 | 3 | 2 | 1 | 0 | 1 | 4 | — | 0 | — |
| 2 | 1.0 | Pre | 4 | 4 | 2 | 4 | 2 | 5 | 5 | 4 | 0 | 5 | 3 | 5 |
| | | Post | 2 | 2 | 2 | 3 | 3 | 2 | 2 | 2 | 2 | 2 | 2 | 3 |
| 4 | 1.0 | Pre | 4 | 4 | — | 5 | 3 | 5 | 5 | 4 | 0 | 5 | 4 | 5 |
| | | Post | 2 | 3 | 1 | 3 | 3 | 3 | 0 | 3 | 2 | 2 | 1 | 3 |
| 5 | 1.0 | Pre | 4 | 4 | — | 4 | 4 | 5 | 5 | 3 | 0 | 5 | 3 | 5 |
| | | Post | 0 | 1 | 1 | 3 | 2 | 4 | 0 | 0 | 3 | 1 | 0 | 1 |
| 6 | 1.0 | Pre | 4 | 4 | 1 | 5 | 3 | 5 | 5 | 4 | 0 | — | 5 | 4 |
| | | Post | 3 | 3 | 2 | 3 | 4 | 2 | 0 | 1 | 2 | 2 | 2 | 3 |
| 7 | 1.0 | Pre | 3 | 4 | 0 | 4 | 3 | 3 | 3 | 1 | 0 | — | 5 | 5 |
| | | Post | 3 | 3 | 1 | 3 | 3 | 1 | 0 | 1 | 3 | 2 | 2 | 2 |
| 8 | 5.0 | Pre | 0 | 0 | 0 | 5 | 0 | 0 | 0 | 0 | 0 | — | 0 | 1 |
| | | Post | 0 | 2 | 1 | 2 | 1 | 0 | 0 | 0 | 2 | 1 | 0 | 3 |
| 10 | 1.0 | Pre | 4 | 4 | 3 | 5 | 4 | 4 | 5 | 4 | 0 | — | — | 0 |
| | | Post | 2 | 0 | 1 | 0 | 3 | 4 | 2 | 2 | 3 | 4 | 0 | 0 |
| 12 | 5.0 | Pre | 0 | — | 0 | 4 | 0 | 0 | 0 | 0 | 0 | — | 0 | 0 |
| | | Post | 0 | 0 | 0 | 2 | 0 | 1 | 0 | 0 | 2 | 2 | 0 | 1 |
| 14 | 5.0 | Pre | 0 | — | 0 | 4 | 2 | 0 | 0 | 1 | 0 | 0 | 0 | 0 |
| | | Post | 0 | 1 | 0 | 3 | 0 | 0 | 0 | 0 | 1 | 0 | 0 | 0 |
| 15 | 5.0 | Pre | 0 | — | 0 | 4 | 0 | 1 | 0 | 0 | 0 | 5 | 0 | 0 |
| | | Post | 0 | 0 | 1 | 3 | 2 | 0 | 0 | 0 | 3 | 1 | 0 | 0 |
| 16 | 1.0 | Pre | 3 | 3 | 0 | 4 | 1 | 2 | 4 | 3 | 0 | 5 | 3 | 4 |
| | | Post | 3 | 3 | 2 | 3 | 1 | 0 | 0 | 3 | 3 | 3 | 2 | 3 |
| 19 | 1.0 | Pre | 1 | 3 | 0 | 4 | 0 | 1 | 1 | 2 | 1 | 5 | 0 | 0 |
| 20 | 1.0 | Pre | 3 | 4 | 3 | 5 | 3 | 5 | 3 | 3 | 0 | 5 | 0 | 4 |
| | | Post | 2 | 2 | 1 | 2 | 0 | 0 | 0 | 1 | 2 | 2 | 0 | 2 |
| 21 | 2.0 | Pre | 3 | 3 | 0 | 4 | 1 | 3 | 3 | 3 | 4 | 5 | — | 0 |
| 22 | 5.0 | Pre | 5 | 4 | 0 | 5 | 3 | 4 | 4 | 0 | 0 | 5 | — | 3 |
| | | Post | 1 | 0 | 0 | 3 | 1 | 0 | 0 | 0 | 0 | 3 | — | 1 |
| 23 | 5.0 | Pre | 0 | 3 | 3 | 4 | 3 | 5 | 4 | — | 1 | 0 | 0 | 0 |
| 24 | 5.0 | Pre | 4 | 3 | 2 | — | 0 | 3 | 4 | 1 | 3 | 2 | — | 2 |
| 25 | 5.0 | Pre | 0 | 0 | 0 | — | 0 | 3 | 0 | 1 | 2 | 2 | — | 1 |
| 28 | 5.0 | Pre | 2 | 3 | 2 | 1 | 0 | 2 | 0 | 0 | 2 | 0 | — | 0 |

| | | | Po | Xs | Ab | Cv | Ot/Av | Dg | Pu | St | Ec | Sh | Ag | Cn |
|---|---|---|---|---|---|---|---|---|---|---|---|---|---|---|
| 1 | 1.0 | Pre | 2 | 1 | 4 | — | 3 | 5 | 5 | 4 | 3 | 0 | 2 | 2 |
| | | Post | 0 | 0 | 2 | — | 1 | 4 | 0 | 2 | 4 | 1 | 0 | 0 |
| 2 | 1.0 | Pre | 5 | 0 | 5 | — | 4 | 5 | 5 | 5 | 5 | 5 | 0 | 5 |
| | | Post | 3 | 1 | 3 | — | 1 | 4 | 2 | 4 | 2 | 0 | 0 | 0 |
| 4 | 1.0 | Pre | — | 1 | 4 | — | 4 | 5 | — | 5 | 5 | 4 | 0 | 0 |
| | | Post | — | 2 | 2 | — | 4 | 4 | — | 4 | 2 | 2 | 0 | 0 |
| 5 | 1.0 | Pre | — | 0 | 4 | — | 5 | 5 | — | 5 | 5 | 4 | 3 | 2 |
| | | Post | — | 1 | 2 | — | 3 | 4 | — | 2 | 1 | 1 | 0 | 0 |
| 6 | 1.0 | Pre | — | 0 | 4 | — | 4 | 5 | — | 5 | 5 | 3 | 0 | — |
| | | Post | — | 1 | 3 | — | 3 | 3 | — | 4 | 1 | 1 | 0 | 0 |
| 7 | 1.0 | Pre | — | 0 | 4 | — | 3 | 5 | — | 4 | 5 | 0 | 1 | — |
| | | Post | — | 1 | 2 | — | 1 | 4 | — | 3 | 0 | 0 | 0 | 0 |
| 8 | 5.0 | Pre | — | 0 | 4 | — | 1 | 3 | — | 0 | 4 | 2 | 1 | 0 |
| | | Post | — | 0 | 0 | — | 0 | 2 | — | 3 | 2 | 1 | 0 | 0 |
| 10 | 1.0 | Pre | — | 0 | 4 | — | 5 | 5 | — | 5 | 5 | 2 | 2 | 5 |
| | | Post | — | 0 | 3 | — | 4 | 4 | — | 3 | 0 | 2 | 0 | 3 |
| 12 | 5.0 | Pre | — | 0 | — | — | 4 | 0 | — | 0 | 0 | 2 | 0 | 1 |
| | | Post | — | 0 | 1 | — | 0 | 0 | — | 0 | 0 | 1 | 0 | 0 |
| 14 | 5.0 | Pre | — | 0 | 0 | — | 1 | 0 | — | 0 | 4 | 0 | 0 | — |
| | | Post | — | 0 | 0 | — | 0 | 0 | — | 0 | 0 | 0 | 1 | 0 |
| 15 | 5.0 | Pre | — | 0 | 2 | — | 3 | 0 | — | 0 | 4 | 0 | 0 | — |
| | | Post | — | 0 | 2 | — | 0 | 0 | — | 0 | 2 | 1 | 0 | 0 |
| 16 | 1.0 | Pre | — | 0 | 2 | — | 3 | 5 | — | 3 | 2 | 0 | 0 | — |
| | | Post | — | 2 | 3 | — | 1 | 4 | — | 3 | 3 | 3 | 0 | — |
| 19 | 1.0 | Pre | — | 1 | 3 | — | 2 | 5 | — | 3 | 2 | 0 | 0 | 0 |
| 20 | 1.0 | Pre | — | 0 | 4 | — | 4 | 5 | — | 5 | 5 | 2 | 0 | 0 |
| | | Post | — | 1 | 2 | — | 0 | 3 | — | 1 | 1 | 1 | 0 | 0 |
| 21 | 2.0 | Pre | — | 0 | 4 | — | 3 | 5 | — | 5 | 5 | 5 | 0 | — |
| 22 | 5.0 | Pre | — | 0 | 4 | 0 | 1 | 5 | 4 | 5 | 5 | 4 | 3 | — |
| | | Post | 3 | 0 | 0 | 0 | 0 | 0 | 0 | 3 | 0 | 0 | 0 | — |

TABLE 2-continued

| COMPOUND NO | RATE OF APPLICATION kg/ha | PRE- OR POST-EMERGENCE APPLICATION | TEST PLANTS | | | | | | | | | | | |
|---|---|---|---|---|---|---|---|---|---|---|---|---|---|---|
| 23 | 5.0 | Pre | — | 0 | 5 | 4 | 5 | 1 | 5 | 5 | 5 | 4 | 5 | 1 |
| 24 | 5.0 | Pre | 1 | 0 | 5 | 4 | 5 | 2 | 4 | 5 | 3 | 1 | 3 | 2 |
| 25 | 5.0 | Pre | 1 | — | 2 | 1 | 3 | 0 | 2 | 0 | 0 | 0 | 0 | 0 |
| 28 | 5.0 | Pre | — | 0 | 5 | 3 | 2 | 1 | 4 | 0 | 5 | 2 | 1 | 0 |

TABLE 3

| COMPOUND NO | RATE OF APPLICATION kg/ha | PRE- OR POST-EMERGENCE APPLICATION | TEST PLANTS | | | | | | | | | | | |
|---|---|---|---|---|---|---|---|---|---|---|---|---|---|---|
| | | | Sb | Rp | Ct | Sy | Mz | Ww | Rc | Sn | Ip | Am | Pi | Ca |
| 29 | 5.0 | Pre | — | — | — | — | — | 0 | — | — | — | — | — | — |
| 30 | 5.0 | Pre | 3 | 3 | 1 | 4 | 3 | 4 | 5 | 0 | 3 | 0 | — | 0 |
| | | Post | 2 | 2 | 1 | 0 | 2 | 2 | 1 | 3 | 3 | — | — | — |
| 31 | 5.0 | Pre | 3 | 4 | 0 | 3 | 0 | 1 | 0 | 4 | 0 | 0 | — | 0 |
| | | Post | 1 | 3 | 0 | 0 | 4 | 0 | 0 | 3 | 2 | 0 | — | 2 |
| 32 | 0.2 | Pre | 4 | 5 | 2 | 5 | 2 | 2 | 4 | 5 | 3 | 2 | — | 0 |
| 32 | 1.0 | Pre | 5 | 5 | 3 | 5 | 5 | 5 | 5 | 5 | 4 | 4 | — | 1 |
| | | Post | 3 | 3 | 1 | 1 | 4 | 4 | 3 | 3 | 3 | 2 | — | 2 |
| 33 | 1.0 | Pre | 4 | 4 | 1 | 4 | 3 | 3 | 3 | 0 | 3 | 1 | — | 2 |
| | | Post | 1 | 0 | 2 | 2 | 0 | 0 | 0 | 0 | 0 | 1 | — | 1 |
| 34 | 5.0 | Pre | 1 | 3 | 1 | — | 1 | 1 | 0 | 3 | 1 | 1 | — | — |
| 35 | 1.0 | Pre | 4 | 4 | — | 4 | 2 | 3 | 5 | 4 | 4 | 4 | 1 | 1 |
| | | Post | 0 | — | 0 | 0 | 3 | 3 | 0 | 0 | 3 | — | 2 | 4 |
| 36 | 5.0 | Pre | 4 | 4 | 1 | 3 | 1 | 2 | 3 | 0 | 4 | 1 | 1 | 2 |
| | | Post | 0 | 0 | 0 | 1 | 1 | 0 | 0 | 0 | 2 | 1 | — | 2 |
| 37 | 1.0 | Pre | 5 | 5 | 0 | 0 | 0 | 0 | 0 | 4 | 2 | 3 | 1 | 5 |
| | | Post | 1 | 0 | 2 | 2 | 0 | 0 | 0 | 3 | 2 | — | 1 | 3 |
| 38 | 1.0 | Pre | 4 | 3 | 5 | 1 | 1 | 1 | 1 | 3 | 2 | 4 | 1 | 4 |
| | | Post | 2 | 3 | 2 | 2 | 1 | 0 | 0 | 3 | 2 | — | 1 | 3 |
| 39 | 1.0 | Pre | 1 | 1 | 0 | 1 | 0 | 1 | 1 | 1 | 0 | 0 | 0 | 0 |
| | | Post | 1 | 0 | 0 | 0 | 0 | 0 | 0 | 0 | 0 | — | 0 | 0 |

| COMPOUND NO | RATE OF APPLICATION kg/ha | PRE- OR POST-EMERGENCE APPLICATION | TEST PLANTS | | | | | | | | | | | |
|---|---|---|---|---|---|---|---|---|---|---|---|---|---|---|
| | | | Ga | Xa | Ab | Co | Av | Dg | Al | St | Ec | Sh | Ag | Cn |
| 29 | 5.0 | Pre | — | — | 3 | — | — | — | — | — | — | — | — | — |
| 30 | 5.0 | Pre | — | 0 | 5 | 4 | 5 | 3 | 3 | 5 | 5 | 4 | 5 | 1 |
| | | Post | 1 | 0 | 2 | 1 | 2 | 0 | — | — | 0 | 2 | 1 | 0 |
| 31 | 5.0 | Pre | — | 0 | 2 | 0 | 2 | 0 | 2 | 2 | 0 | 0 | 0 | 0 |
| | | Post | 2 | 1 | 0 | 1 | 1 | 1 | — | — | 0 | 0 | 0 | 0 |
| 32 | 0.2 | Pre | — | 0 | 5 | 4 | 5 | 3 | 4 | 5 | 5 | 2 | 2 | 3 |
| 32 | 1.0 | Pre | — | 2 | 5 | 4 | 5 | 3 | 5 | 5 | 5 | 4 | 5 | 3 |
| | | Post | 3 | 2 | 3 | 3 | 4 | 4 | — | — | 3 | 4 | 2 | 3 |
| 33 | 1.0 | Pre | — | 5 | 5 | 3 | 4 | 3 | 5 | 5 | 5 | 3 | 5 | 3 |
| | | Post | 1 | 0 | 2 | 0 | 1 | 0 | 0 | 1 | 0 | 1 | 0 | 0 |
| 34 | 5.0 | Pre | 0 | — | 5 | 2 | 1 | 0 | 2 | 3 | 1 | 2 | 0 | 2 |
| 35 | 1.0 | Pre | 0 | 0 | — | 5 | 4 | 4 | 5 | 5 | 5 | 3 | 5 | 3 |
| | | Post | 0 | 0 | 2 | 3 | 4 | 0 | — | 2 | 3 | 3 | 2 | 2 |
| 36 | 5.0 | Pre | — | — | 4 | 4 | 4 | 5 | 1 | 5 | 5 | 4 | 5 | 4 |
| | | Post | 0 | 0 | 1 | 0 | 0 | 3 | 0 | 0 | 2 | 0 | 1 | 0 |
| 37 | 1.0 | Pre | 0 | 0 | 4 | 2 | 0 | 0 | 0 | 3 | 1 | 1 | 0 | 0 |
| | | Post | 0 | 1 | 0 | 2 | — | 2 | 0 | 2 | 1 | 3 | 0 | 0 |
| 38 | 1.0 | Pre | 0 | 1 | 2 | 1 | 0 | 0 | 1 | 1 | 0 | 0 | 0 | 0 |
| | | Post | 0 | 1 | 1 | 1 | 0 | 1 | 0 | 0 | 1 | 1 | — | 0 |
| 39 | 1.0 | Pre | 0 | 0 | 2 | 0 | 0 | 0 | 0 | 0 | 0 | 0 | 0 | 0 |
| | | Post | 0 | 0 | 1 | 1 | 0 | 0 | 0 | 0 | 0 | 0 | — | 0 |

| Names of test plants in Tables 2 and 3 | |
|---|---|
| Sb | Sugar beet |
| Rp | Rape |
| Ct | Cotton |
| Sy | Soya Bean |
| Mz | Maize |
| Ww | Winter wheat |
| Rc | Rice |
| Sn | Senecio vulgaris |
| Ip | Ipomoea purpurea |
| Am | Amaranthus retroflexus |
| Pi | Polygonum aviculare |
| Ca | Chenopodium album |
| Po | Portulaca oleracea |
| Xs and Xa | Xanthium spinosum |
| Ab | Abutilon theophrastii |
| Cv | Convolvulus arvensis |
| Ot/Av | Oats (cultivated in pre-emergence test and Avena fatua (wild oats) in post-emergence test) (Applies to Table 2; in Table 3 only Avena fatua is used) |
| Dg | Digitaria sanguinalis |
| Pu | Poa annua |
| St | Setaria viridis |
| Ec | Echinochloa crus-galli |
| Sh | Sorghum halepense |
| Ag | Agropyron repens |
| Cn | Cyperus rotundus |
| Ga | Galium aparine |
| Co | Cassia obtusifolia |

-continued

| Names of test plants in Tables 2 and 3 | |
|---|---|
| A1 | *Alopecurus myosuroides* |

EXAMPLE 7

This Example illustrates a composition according to the invention which comprises an emulsifiable concentrate. The following ingredients were thoroughly mixed to give a solution.

| | |
|---|---|
| Compound No. 1 of Table I | 10% |
| Ethylene dichloride | 40% |
| Calcium dodecylbenzenesulphate | 5% |
| "Lubrol" L | 10% |
| "Aromasol" H | 35% |

EXAMPLE 8

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44–100, to obtain the desired size of grains.

| | |
|---|---|
| Compound No. 2 of Table I | 50% |
| "Dispersol" T | 25% |
| "Lubrol" APN 5 | 1.5% |
| Sodium acetate | 23.5% |

EXAMPLE 9

The following ingredients were ground together to produce a powder formulation readily dispersible in liquids.

| | |
|---|---|
| Compound No. 8 of Table I | 45% |
| "Dispersol" T | 5% |
| "Lissapol" NX | 0.5% |
| "Cellofas" B600 | 2% |
| Sodium acetate | 47.5% |

EXAMPLE 10

The active ingredient was dissolved in acetone and the resultant liquid was sprayed on to the granules of china clay. The solvent was then allowed to evaporate to produce a granular composition.

| | |
|---|---|
| Compound No. 9 of Table I | 5% |
| China clay granules | 95% |

EXAMPLE 11

A composition suitable for use as a seed dressing was prepared by mixing the following three ingredients.

| | |
|---|---|
| Compound No. 1 of Table I | 50% |
| Mineral oil | 2% |
| China clay | 48% |

EXAMPLE 12

A dusting powder was prepared by mixing the active ingredient with talc.

| | |
|---|---|
| Compound No. 1 of Table I | 5% |
| Talc | 95% |

EXAMPLE 13

A flowable formulation was prepared by ball-milling the constituents set out below and then forming an aqueous suspension of the ground mixture with water.

| | |
|---|---|
| Compound No. 8 of Table I | 40% |
| "Dispersol" T | 10% |
| "Lubrol" APN5 | 1% |
| Water | 49% |

EXAMPLE 14

A dispersible powder formulation was made by mixing together the ingredients set out below and then grinding the mixture until all were thoroughly mixed.

| | |
|---|---|
| Compound No. 9 of Table I | 25% |
| "Aerosol" OT/B | 2% |
| "Dispersol" A.C. | 5% |
| China clay | 28% |
| Silica | 40% |

EXAMPLE 15

This Example illustrates the preparation of a dispersible powder formulation. The ingredients were mixed and the mixture then ground in a comminution mill.

| | |
|---|---|
| Compound No. 10 of Table I | 25% |
| "PERMINAL" BX | 1% |
| "Dispersol" T | 5% |
| Polyvinylpyrrolidone | 10% |
| Silica | 25% |
| China clay | 34% |

EXAMPLE 16

The ingredients set out below were formulated into a dispersible powder by mixing then grinding the ingredients.

| | |
|---|---|
| Compound No. 1 of Table I | 25% |
| "Aerosol" OT/B | 2% |
| "Dispersol" A | 5% |
| China clay | 68% |

In Examples 7 to 16 the proportions of the ingredients given are by weight and the Examples were all repeated using, as active ingredient, the other compounds of Table I.

There now follows an explanation of the compositions or substances represented by the various Trade Marks and Trade Names mentioned above.

| | |
|---|---|
| LUBROL L: | a condensate of nonyl phenol (1 mole) with ethylene oxide |

-continued

| | |
|---|---|
| | (13 moles). |
| AROMASOL H: | a solvent mixture of alkyl-benzenes |
| DISPERSOL T AND AC: | a mixture of sodium sulphate and a condensate of formaldehyde with sodium naphthalene sulphonate |
| LUBROL APN 5: | a condensate of nonyl phenol (1 mole) with ethylene oxide (5.5 moles) |
| CELLOFAS B600: | a sodium carboxymethyl cellulose thickener. |

EXAMPLE 17

The compounds were tested against a variety of foliar fungal diseases of paints. The techniques employed were as follows:

The plants were grown in John Innes Potting Compost (No. 1 or 2) in 4 cm diameter mini-pots. A layer of fine sand was placed at the bottom to facilitate uptake of test compound by the roots. The test compounds were formulated either by bead milling with aqueous Dispersol T or as a solution in acetone or acetone/ethanol which was diluted to the required concentration immediately before use. For the foliage diseases suspensions (100 ppm active ingredient) were sprayed on to the foliage and applied to the roots of the same plant via the soil. An exception were the test on *Botrytis cinerea*, *Plasmopara viticola*, and *Venturia inaequalis* in which the compound was sprayed on to the foliage only. Sprays were applied to maximum retention, and root drenches were applied to a final concentration equivalent to approximately 40 ppm a.i./dry soil. Tween 20, to give a final concentration of 0.05% was added when the sprays were applied to cereals.

For most of the tests the compound was applied to the soil (roots) and to the foliage (by spraying) one or two days before the plant was inoculated with the diseases. An exception was the test on *Erysiphe graminis* in which the plants were inoculated 24 hours before treatment. After inoculation, the plants were put into an appropriate environment to allow infection to take place and then incubated until the disease was ready for assessment.

The period between inoculation and assessment varied from four to fourteen days according to the disease and environment.

The disease control was recorded by the following grading:

| |
|---|
| 4 = no disease |
| 3 = trace - 5% of disease on untreated plants |
| 2 = 6–25% of disease on untreated plants |
| 1 = 26–59% of disease on untreated plants |
| 0 = 60–100% of disease on untreated plants |

The results are shown in Table 4 below.

A dash, thus "—", in the table in any column indicates that the particular compound was not tested against that particular disease.

An asterisk, thus "*" against the disease grading in the column headed "*BOTRYTIS CINEREA* (TOMATO)" signifies that the test plant material used in this instance was grape berries.

TABLE 4

| COMPOUND NUMBER | PUCCINIA RECONDITA (WHEAT) | ERYSIPHE GRAMINIS (BARLEY) | PLASMOPARA VITICOLA (VINE) | PHYTOPHTHORA INFESTANS (TOMATO) | BOTRYTIS CINEREA (TOMATO) | CERCOSPORA ARACHIDICOLA (PEANUT) | VENTURIA INAEQUALIS (APPLE) |
|---|---|---|---|---|---|---|---|
| 1 | 0 | 0 | 4 | 4 | 0 | — | — |
| 2 | 0 | 0 | 4 | 4 | 2 | — | — |
| 3 | 0 | 0 | 1 | — | 2 | — | — |
| 4 | 1 | 0 | — | 0 | 0 | 3 | 0 |
| 5 | 0 | 1 | — | 3 | 0 | 3 | 0 |
| 6 | 0 | 0 | 4 | 0 | 0 | 0 | 0 |
| 7 | 0 | 0 | 4 | 3 | 0 | 2 | 1 |
| 8 | 0 | 0 | 0 | 1 | 0 | 0 | 1 |
| 9 | 0 | 0 | 0 | 0 | 1 | 0 | 0 |
| 10 | 0 | 0 | 4 | 4 | 0 | 1 | 0 |
| 11 | 0 | 0 | 0 | 0 | 0 | 0 | 0 |
| 12 | 0 | 0 | 0 | 0 | 0 | 2 | 0 |
| 13 | — | — | — | — | — | — | — |
| 14 | 0 | 0 | 0 | 0 | 0 | 0 | 0 |
| 15 | 0 | 0 | 0 | 0 | 0 | 0 | 0 |
| 16 | 0 | 0 | 4 | 3 | 0 | 0 | 0 |
| 17 | 0 | 0 | 4 | 4 | 0 | 1 | 0 |
| 18 | 0 | 0 | 4 | 4 | 0 | 2 | 0 |
| 19 | — | — | — | — | — | — | — |
| 20 | 0 | 0 | 4 | 4 | 0 | 3 | 0 |
| 21 | 0 | 2 | 4 | 4 | 0 | 0 | 0 |
| 22 | 0 | 0 | 4 | 3 | 0 | 1 | 0 |
| 23 | 0 | 0 | 4 | 4 | 0 | 0 | 0 |
| 24 | 0 | 0 | 4 | 4 | 0 | 0 | 2 |
| 25 | 0 | 0 | 0 | 0 | 0 | 1 | 0 |
| 26 | 0 | 0 | 4 | 0 | 0 | 0 | 0 |
| 27 | 0 | 0 | 0 | 0 | 0 | 0 | 0 |
| 28 | 0 | 0 | 0 | 0 | 0 | 1 | 0 |
| 29 | 0 | 0 | 0 | 0 | 0 | 0 | 0 |
| 30 | 0 | 0 | 3 | 3 | 1 | 1 | 0 |
| 31 | 3 | 4 | 3 | 3 | 0 | 0 | 0 |
| 32 | 0 | 0 | 4 | 3 | 0 | 1 | 0 |
| 33 | 0 | 0 | 4 | 4 | 0 | 3 | 2 |
| 34 | 0 | 0 | 4 | 3 | 0* | 0 | 0 |
| 35 | — | 0 | 4 | 4 | 0* | 0 | — |
| 36 | 0 | 0 | 3 | — | 0* | — | — |
| 37 | 0 | 0 | 0 | 0 | 0* | 0 | 0 |

TABLE 4-continued

| COMPOUND NUMBER | PUCCINIA RECONDITA (WHEAT) | ERYSIPHE GRAMINIS (BARLEY) | PLASMOPARA VITICOLA (VINE) | PHYTOPHTHORA INFESTANS (TOMATO) | BOTRYTIS CINEREA (TOMATO) | CERCOSPORA ARACHIDICOLA (PEANUT) | VENTURIA INAEQUALIS (APPLE) |
|---|---|---|---|---|---|---|---|
| 38 | 0 | 0 | 0 | 0 | 0* | 1 | 0 |
| 39 | 0 | 1 | 4 | 3 | 0* | 0 | 0 |
| 40 | 0 | 2 | 0 | 0 | 0* | 0 | 0 |
| 41 | 0 | 1 | 0 | 0 | 0* | 0 | 0 |
| 42 | 0 | 0 | 3 | 2 | 0* | 0 | 0 |
| 43 | 0 | 0 | 0 | 0 | 0* | 0 | 0 |
| 44 | 0 | 1 | 3 | 1 | 0* | 0 | 2 |
| 45 | 1 | 0 | 0 | 1 | 0* | 1 | 0 |
| 46 | 0 | 0 | 4 | 3 | 0 | 4 | 0 |
| 47 | 0 | 4 | 4 | 3 | 0 | 2 | 3 |
| 48 | 0 | 0 | 0 | 0 | 0 | 0 | 0 |
| 49 | 0 | 3 | 4 | — | 0 | 1 | — |
| 50 | 0 | 2 | 4 | — | 0 | 0 | 0 |
| 51 | 0 | 0 | 4 | — | 0 | 0 | 0 |
| 52 | 0 | 0 | 3 | — | 0 | 0 | 0 |
| 53 | 0 | 2 | 4 | — | 0 | 0 | 0 |
| 54 | 0 | 1 | 4 | — | 0 | 0 | 0 |
| 55 | 0 | 0 | 4 | — | 0 | 1 | 0 |
| 56 | 0 | 0 | 4 | — | 0 | 0 | 0 |
| 57 | 0 | 0 | 4 | — | — | 0 | 0 |
| 58 | 0 | 0 | 1 | — | 0 | 0 | 4 |
| 59 | — | 0 | 0 | — | 0 | 1 | 0 |
| 60 | 0 | 0 | 0 | — | 0 | 0 | 0 |
| 61 | 0 | 2 | 4 | — | 0 | 0 | 0 |
| 62 | 0 | 0 | 0 | — | 0 | 0 | 0 |
| 63 | 0 | 2 | 1 | — | 0 | 0 | 0 |
| 64 | 0 | 0 | 4 | — | 0 | 0 | 1 |
| 65 | 0 | 0 | 1 | — | 1 | 0 | 0 |

"—" means not tested
*means test plant material used was grape berries instead of tomato plants

We claim:
1. A compound of the formula

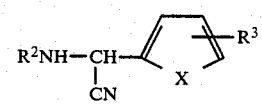

where $R^2$ is alkenyl of 3 to 5 carbon atoms either unsubstituted or substituted with $C_1$-$C_4$ alkoxy, $C_1$-$C_4$ alkylthio, or halogen, X is oxygen or sulphur, and $R^3$ is hydrogen, $C_{1-4}$ alkyl or halogen.

* * * * *